US008349363B2

(12) United States Patent (10) Patent No.: US 8,349,363 B2
Huang et al. (45) Date of Patent: Jan. 8, 2013

(54) TEMPERATURE RESPONSIVE DELIVERY SYSTEMS

(75) Inventors: Yanbin Huang, Roswell, GA (US); Bashir Musse Sheikh-Ali, Duluth, GA (US); Jaeho Kim, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 858 days.

(21) Appl. No.: 12/266,782

(22) Filed: Nov. 7, 2008

(65) Prior Publication Data
US 2009/0117075 A1 May 7, 2009

Related U.S. Application Data

(62) Division of application No. 10/135,805, filed on Apr. 30, 2002, now abandoned.

(51) Int. Cl.
*A61K 9/14* (2006.01)
*A61K 8/02* (2006.01)
*A61K 31/765* (2006.01)
*A61K 47/32* (2006.01)
*A61K 47/30* (2006.01)

(52) U.S. Cl. ............ 424/486; 424/401; 424/78.38; 514/772.4; 514/772.6; 514/772.3

(58) Field of Classification Search ............ 424/486, 424/401, 78.38, 85.4; 514/772.4, 772.6, 514/772.3
See application file for complete search history.

(56) References Cited

U.S. PATENT DOCUMENTS

| | | | |
|---|---|---|---|
| 2,828,345 A | 3/1958 | Spriggs | |
| 2,961,347 A | 11/1960 | Floyd | |
| 3,227,615 A | 1/1966 | Korden | |
| 3,949,014 A | 4/1976 | Maki et al. | |
| 4,082,705 A | 4/1978 | Beede et al. | |
| 4,140,763 A | 2/1979 | Bachrach et al. | |
| 4,188,373 A | 2/1980 | Krezanoski | |
| 4,301,067 A | 11/1981 | Koshugi | |
| 4,347,339 A | 8/1982 | Boevink et al. | |
| 4,369,037 A | 1/1983 | Matsunaga et al. | |
| 4,554,174 A | 11/1985 | Ohta et al. | |
| 4,673,704 A | 6/1987 | Flesher et al. | |
| 4,678,606 A * | 7/1987 | Akhter et al. ............ | 510/159 |
| 4,710,374 A | 12/1987 | Grollier et al. | |
| 4,764,365 A * | 8/1988 | Boothe et al. ............ | 514/772.6 |
| 4,810,503 A | 3/1989 | Carson et al. | |
| 4,830,776 A | 5/1989 | Thompson | |
| 4,835,206 A | 5/1989 | Farrar et al. | |
| 4,839,166 A | 6/1989 | Grollier et al. | |
| 4,857,303 A | 8/1989 | Grollier | |
| 4,888,168 A | 12/1989 | Potts et al. | |
| 4,894,237 A | 1/1990 | Bellani et al. | |
| 4,983,392 A | 1/1991 | Robinson | |
| 5,013,763 A | 5/1991 | Tubesing et al. | |
| 5,100,951 A | 3/1992 | Fillipo et al. | |
| 5,112,886 A | 5/1992 | Phalangas | |
| 5,143,731 A | 9/1992 | Viegas et al. | |
| 5,225,196 A | 7/1993 | Robinson | |
| 5,252,318 A | 10/1993 | Joshi et al. | |
| 5,275,809 A | 1/1994 | Chen et al. | |
| 5,296,218 A | 3/1994 | Chen et al. | |
| 5,338,541 A | 8/1994 | Matz et al. | |
| 5,441,732 A | 8/1995 | Hoeg et al. | |
| 5,456,923 A | 10/1995 | Nakamichi et al. | |
| 5,474,768 A | 12/1995 | Robinson | |
| 5,562,898 A * | 10/1996 | Dowell et al. ............ | 424/70.1 |
| 5,569,686 A | 10/1996 | Makati et al. | |
| 5,587,175 A | 12/1996 | Viegas et al. | |
| 5,614,178 A | 3/1997 | Bloom et al. | |
| 5,618,560 A | 4/1997 | Bar-Shalom et al. | |
| 5,641,809 A | 6/1997 | Hagen et al. | |
| 5,643,582 A | 7/1997 | Gangadharan et al. | |
| 5,656,258 A | 8/1997 | Cauwet et al. | |
| 5,833,965 A | 11/1998 | Sun et al. | |
| 5,876,744 A | 3/1999 | Della Valle et al. | |
| 5,939,485 A | 8/1999 | Bromberg et al. | |
| 5,968,500 A | 10/1999 | Robinson | |
| 5,980,868 A | 11/1999 | Homola et al. | |
| 6,004,573 A | 12/1999 | Rathi et al. | |
| 6,017,521 A | 1/2000 | Robinson et al. | |
| 6,033,680 A | 3/2000 | Dixon et al. | |
| 6,068,924 A | 5/2000 | Palumbo | |
| 6,072,101 A | 6/2000 | Beihoffer et al. | |
| 6,084,045 A | 7/2000 | Fornasari et al. | |
| 6,113,882 A | 9/2000 | Mougin et al. | |

(Continued)

FOREIGN PATENT DOCUMENTS

| | | |
|---|---|---|
| CN | 1145080 | 3/1997 |
| EP | 0470703 | 2/1992 |
| EP | 0 818 194 A2 | 1/1998 |
| GB | 722746 | 1/1955 |
| WO | WO 95/24430 | 9/1995 |
| WO | WO 97/05185 * | 2/1997 |
| WO | WO 97/34580 | 9/1997 |
| WO | WO 99/01716 | 1/1999 |
| WO | WO 01/41821 | 6/2001 |

OTHER PUBLICATIONS

Martin Malmsten and Bjorn Lindman, *Macromolecules* 1993, 26, Effects of Homopolymers on the Gel Formation in Aqueous Block Copolymer Solutions, o. 1282-1286.
Byeongmoon Jeong, Merinda R. Kibbey, Jerome C. Birnbaum, You-Yeon Won, and Anna Gutowska, *Macromolecules* 2000, 33, Thermogelling Biodegradable Polymers with Hydrophilic Backbones: PEG-g-PLGA, p. 8317-8322.

*Primary Examiner* — Blessing Fubara
(74) *Attorney, Agent, or Firm* — Dority & Manning, P.A.

(57) ABSTRACT

There is provided a new aqueous temperature responsive delivery system made with a temperature responsive polymer and a bioadhesive which is intrinsically cationic. This system may also have an effective amount of a treating agent, which may be a medical or cosmetic agent. The bioadhesive, temperature responsive delivery system is useful in delivering moisturizers or pharmaceutically active agents to the user in controlled release manners, through the tissues in a body cavity.

18 Claims, No Drawings

U.S. PATENT DOCUMENTS

| | | |
|---|---|---|
| 6,139,848 A | 10/2000 | Ahmad et al. |
| 6,143,352 A | 11/2000 | Clark et al. |
| 6,159,591 A | 12/2000 | Beihoffer et al. |
| 6,183,732 B1 | 2/2001 | Salmon |
| 6,197,331 B1 | 3/2001 | Lerner et al. |
| 6,201,072 B1 | 3/2001 | Rathi et al. |
| 6,229,062 B1 | 5/2001 | Mandell et al. |
| 6,235,965 B1 | 5/2001 | Beihoffer et al. |
| 6,245,197 B1 | 6/2001 | Oriaran et al. |
| 6,258,873 B1 * | 7/2001 | Gundlach et al. ............. 523/160 |
| 6,258,996 B1 | 7/2001 | Goldman |
| 6,306,243 B1 | 10/2001 | Clark et al. |
| 6,319,520 B1 | 11/2001 | Wuthrich et al. |
| 6,323,306 B1 | 11/2001 | Song et al. |
| 6,338,842 B1 | 1/2002 | Restle et al. |
| 6,486,213 B1 | 11/2002 | Chen et al. |
| 6,503,519 B1 * | 1/2003 | Sakuta .......................... 424/401 |

* cited by examiner

TEMPERATURE RESPONSIVE DELIVERY SYSTEMS

PRIORITY INFORMATION

The present application claims priority to and is a divisional application of U.S. patent application Ser. No. 10/135,805 filed on Apr. 30, 2002, which is incorporated herein by reference.

BACKGROUND OF THE INVENTION

The present invention concerns the delivery of treating agents and moisturizers to the body.

Moisturizers are used for the treatment of dryness and the symptoms related to it in areas such as, for example the vaginal cavity. The current technologies for moisturizers include the use of a hydrophobic barrier such as petrolatum, mineral oil or lanolin to cover the affected tissue. Another method deploys a humectant such as glycerol or propylene glycol and yet a third uses synthetic or natural polymers like polyacrylic acid and hyaluronic acid.

While the current methods may solve some of the problems associated with the delivery of moisturizers to bodily cavities, they do not simultaneously address all of the basic requirements of a successful system. The basic requirements are that the system be effective, perform well in terms of ease of application, coverage, durability of effects, that it be leak resistant and comfortable, and that the system have the capability of delivering other treating agents over time in a controlled release manner.

The hydrophobic barrier approach is not effective for re-moisturizing. Likewise, humectant systems currently available tend to be removed from the body fairly quickly as well. The use of synthetic or natural polymers has proven somewhat effective. The available polymeric systems, however, have not been found to be easy to use nor to provide relatively complete tissue coverage. These systems have also been found to have problems with leakage from the body cavity.

There remains a need, therefore, for a delivery system that may be used by a consumer and which will be effective, perform well and that may be extended to deliver other treating agents.

SUMMARY OF THE INVENTION

In response to the discussed difficulties and problems encountered in the prior art, a new aqueous temperature responsive delivery system made with a temperature responsive polymer and a bioadhesive which is intrinsically cationic has been developed. The system may also contain a salt and other ingredients such as medicaments (treating agents) and moisturizers.

Temperature responsive or "thermogellation" polymer solutions respond to temperature changes, in this case temperature increases, by changing from a liquid to a gel. These polymers may be block copolymers, graft copolymers and homopolymers.

Suitable intrinsically cationic bioadhesives include synthetic polymers having an ammonium group (N+) in the main, pendant or side chain, and modified natural polymers with an ammonium group in a pendant or side chain.

This system may also have an effective amount of a treating agent which may be a medical (pharmaceutically active) or cosmetic agent. Exemplary medicaments include, but are not limited to, agents for treating infections and menstruation disorders, agents for treating cardiovascular conditions, agents for treating internal conditions, agents for treating mental health conditions, anti-inflammatory agents, chemotherapeutic agents, cardiac tonics, expectorants, oral antiseptics, enzymes, birth control agents, ophthalmic treating agents and combinations thereof.

It's desired that the system have a bioadhesive in an amount between a positive amount and 20 weight percent, more particularly between a positive amount and 10 weight percent, and a thermogelling polymer in an amount between about 5 and 50 weight percent, particularly between about 8 and 25 weight percent, more particularly between about 15 and 25 weight percent and the balance water and any medicaments or moisturizers.

DETAILED DESCRIPTION OF THE INVENTION

The delivery of medicaments and moisturizers to parts of the body is important for comfort and medical reasons. Current systems, as described above, have not entirely met the needs of users. The inventors have found novel systems which are long lasting, easy to apply to a larger area, and are able to be used to deliver other agents. Because the systems of this invention are long lasting, they allow for the controlled release of additional treating agents. The controlled release of an active agent; i.e., release of the active agent over a period of time, is an important feature, allowing a relatively constant rate of delivery for the treating agent.

The system of this invention uses an aqueous solution of a temperature responsive polymer and a bioadhesive, and optionally, a medicament and/or moisturizer. This bioadhesive polymer system is in a liquid state when applied but becomes a semi-solid gel in the body cavity by thermogellation. The in-situ gelation of bioadhesive polymers generally may be induced by changes in pH, temperature, ionic composition and other differences between the bodily cavity and the outside environment. The system of this invention is concerned with the gelation of the bioadhesive by temperature, i.e., thermogellation, rather than the other factors, since it is a more general characteristic than the others, i.e.; it doesn't vary as greatly throughout the body as do pH and ionic composition. As used herein, the term "gel" is defined as a solid or semisolid colloid containing a certain quantity of water. The colloidal solution with water is often called a "hydrosol".

Temperature Responsive Polymers

Temperature responsive or thermogellation polymer solutions respond to temperature changes, in this case temperature increases, by changing from a liquid to a gel. The temperature range of interest in the invention is around that of the human body, or about 35° C. Polymers that change state at about this temperature are useful because they will remain in, for example, a body cavity, after they have been delivered. A liquid would not remain in place.

The thermogellation polymers useful in this invention may be block copolymers, graft copolymers and homopolymers.

Block copolymers suitable for use in this system include polyols and those of polyethylene glycol/poly(lactic-co-glyclic) acid. Commercially available block copolymers include PLURONIC® and TETRONIC® from BASF.

Suitable block copolymer compositions include at least one polyoxyalkylene block copolymer of the formula:

$$Y[(A)_n-E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a olyoxyalkylene moiety constituting at least about 60 weight percent of the copolymer, n has a value such that the average molecular weight of A is at least about 500 to about 900, as determined by the hydroxyl number of a hydrophobe base intermediate,

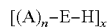 (II)

and the total average molecular weight of the copolymer is at least about 5,000. It should be noted that the term average molecular weight, unless noted otherwise, means the weight average molecular weight.

Generally, the polyoxybutylene-based block copolymers useful in the compositions of the invention are commonly prepared by first condensing 1,2 butylene oxide with a water soluble organic compound initiator containing 1 to about 6 carbon atoms, such as, 1,4 butylene glycol or propylene glycol and at least 2 reactive hydrogen atoms to prepare a polyoxyalkylene polymer hydrophobe of at least about 500, desirably, at least about 1000, most desirably, at least about 1500 average molecular weight. Subsequently, the hydrophobe is capped with an ethylene oxide residue. Specific methods for preparing these compounds are described in U.S. Pat. No. 2,828,345 and British Patent 722,746, both of which are hereby incorporated by reference.

Useful polyoxybutylene based block copolymers conform to the following generic formula:

 (III)

wherein a and b are integers such that the hydrophobe base represented by $(C_4H_8O)$ has a molecular weight of at least about 500, desirably, at least about 1000 and most desirably, at least about 3000, as determined by hydroxyl number, the polyoxyethylene chain constituting at least about 60%, desirably, at least about 70 weight percent of the copolymer and the copolymer having a total average molecular weight of at least about 5000, desirably, at least about 10,000, and more desirably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

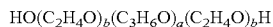 (IV)

wherein a and b are integers such that the hydrophobe base represented by $(C_3H_6O)$ has a molecular weight of at least about 900, desirably, at least about 2500, most desirably, at least about 4000 average molecular weight, as determined by hydroxyl number; the polyoxy-ethylene chain constituting at least about 60%, desirably, at least about 70 weight percent of the copolymer and the copolymer having a total average molecular weight of at least about 5000, desirably, at least about 10,000, and most desirably, at least about 15,000.

Polyoxyethylene-polyoxypropylene block copolymer adducts of ethylene diamine which can be used may be represented by the following formula:

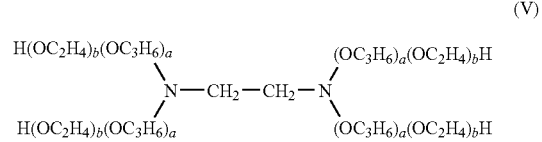 (V)

wherein a and b are integers such that the copolymer may have (1) a hydrophobe base molecular weight of at least about 2000, desirably, at least about 3000, and most desirably, at least about 4500, (2) a hydrophile content of at least about 60%, desirably, at least about 70 weight percent, and (3) a total average molecular weight of at least about 5000, desirably, at least about 10,000, and most desirably, at least about 15,000.

The hydrophobe base of the copolymer of formula V is prepared by adding propylene oxide for reaction at the site of the four reactive hydrogen atoms on the amine groups of ethylene diamine. An ethylene oxide residue is used to cap the hydrophobe base. The hydrophile polyoxyethylene groups are controlled so as to constitute at least about 60%, desirably, at least about 70 weight percent, and more desirably, at least about 80 weight percent of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5 to about 10° C. in water.

When solution is complete the system is brought to room temperature whereupon it forms a gel. If the hot process of forming the gel is used the polymer is added to water heated to a temperature of about 75 to about 85° C. with slow stirring until a clear homogenous solution is obtained. Upon cooling, a clear gel is formed.

The organic compound initiator which is utilized in the process for the preparation of the polyoxyalkylene block copolymers generally is water or an organic compound and can contain a plurality of reactive hydrogen atoms. Desirably, Y in formulas I and II above is defined as derived from a water soluble organic compound having 1 to about 6 carbon atoms and containing x reactive hydrogen atoms where x has a value generally, of at least 1, desirably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylene diamine, and mixtures thereof and the like.

The oxypropylene chains can optionally contain small amounts of at least one of oxyethylene or oxybutylene groups. Oxyethylene chains can optionally contain small amounts of at least one of oxypropylene or oxybutylene groups. Oxybutylene chains can optionally contain small amounts of at least one of oxyethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5,000 to about 50,000, desirably, about 5,000 to about 35,000 and more desirably, about 10,000 to about 25,000.

In addition to those polyoxyalkylene block copolymers referred to above, which are suitable in the formation of the pharmaceutical compositions of the invention, other polyoxyalkylene polymers which form gels at low concentrations in water are suitable. One such polymer is described in U.S. Pat. No. 4,810,503, incorporated herein by reference. These polymers are prepared by capping conventional polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant, which generally do not exceed 10 weight percent total. Detailed methods of preparing these aqueous gels are disclosed in U.S. Pat. No. 4,810,503.

Other suitable polymers are discussed in, for example, U.S. Pat. No. 6,004,573 and is a water soluble biodegradable ABA-type block copolymer made up of a major amount of hydrophobic poly(lactide-co-glycolide) copolymer A-blocks and a minor amount of a hydrophilic polyethylene glycol polymer B-block, having an overall average molecular weight of between about 3100 and 4500. U.S. Pat. No. 6,201,072 teaches a biodegradable ABA- or BAB-type block copolymer having an average molecular weight of between about 2000 and 4990 consisting of about 51 to 83 weight percent of an hydrophobic A polymer block comprising a biodegradable polyester and about 17 to 49 weight percent of a hydrophilic B polymer block consisting of polyethylene glycol (PEG). U.S. Pat. No. 5,939,485 teaches, for example, a 1%, 2% and 3% aqueous temperature responsive polymer network composition comprising a triblock polyol of the general formula (POP)(POE)(POP) and polyacrylic acid (1:1) hydrated and neutralized.

A suitable graft copolymer is one having poly(ethylene glycol) and poly(lactic acid-co-glycolic acid) or PEG-g-PLGA, where the hydrophilic PEG is a backbone. Methods of preparing this graft copolymer are described in "Thermogelling Biodegradable Polymers with Hyrdrophilic Backbones: PEG-g-PLGA" in the journal *Macromolecules,* 2000, 33, 8317-8322. Graft copolymers and their synthesis are also discussed in PCT/US95/02638 (WO 95/24430) which mentions the covalent coupling of a temperature-sensitive component to a backbone polymer.

Cationic Polymer

Most cell and tissue surfaces are negatively charged, so the positively charged bioadhesives of this invention will adhere well to mucosa membranes. It's desired that the bioadhesive adhere primarily to the tissues and not to other ingredients of the system since adhering to other ingredients would not improve it's longevity in contact with the body. The bioadhesives of this invention are pH independent, i.e., intrinsically cationic, polyelectrolytes and positively charged polymers and their crosslinked counterparts. These include synthetic polymers having an ammonium group (N+) in the main chain or as a pendant or side group, and modified natural polymers with an ammonium group in a pendant or side chain. At least one ammonium group should be present in the main chain, desirably more than 1 percent, more desirably more than 5 percent, in the polymers having ammonium groups in the main chain. A pendant group may be a side chain that contains more than one ammonium ion group or a side chain which contains only one ammonium group. Examples of these include:

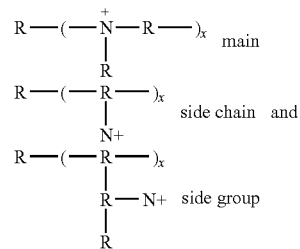

The positively charged polymers may be block copolymers containing a natural polymer block and a synthetic polymer block. The synthetic block of the block copolymer may contain the ammonium group in the main chain or on a pendent group. The pendent group may be a side chain or a side group. The natural block of the block copolymer may contain the ammonium groups on a pendent group that is a side chain or a side group.

Among the cationic polymers, particular examples include polymers of quaternary polyammonium, polyamino amide and polyamine type. Examples of synthetic polymers also include poly(dillyldimethyl ammonium chloride) and poly (dimethylamine-co-epichlorohydrin). Other examples include:

(1) Quaternized or non-quaternized vinylpyrrolidone/dialkylaminoalkyl acrylate or methacrylate copolymers, such as the products sold under the name "GAFQUAT" by the company ISP such as, for example, GAFQUAT® 734, 755 or HS100 or, alternatively, the product known as "Copolymer 937".

(2) Modified cellulose ether derivatives containing quaternary ammonium groups, sold for example by the Union Carbide Corporation. These polymers are also defined in the CTFA dictionary as quaternary ammonium hydroxyethylcellulose that has reacted with an epoxide substituted with a trimethylammonium group.

(3) Modified cationic cellulose derivatives such as cellulose co-polymers or cellulose derivatives grafted with a water-soluble monomer of quaternary ammonium, and described, in particular, in U.S. Pat. No. 4,131,576, incorporated herein by reference, such as hydroxyalkylcellulo-ses, for instance hydroxymethyl-, hydroxyethyl- or hy-droxypropylcelluloses grafted, in particular, with a meth-acryloylethyltrimethylammonium, methacrylamidopropyltrimethylammonium or dimethyldiallylammonium salt. The commercial products corresponding to this definition are, more particularly, the products sold under the names CELQUAT® L 200, CELQUAT® SC-230M, CELQUAT® SC-240C and CELQUAT® H 100 by the National Starch Company.

(4) The cationic polysaccharides as described, more particularly, in U.S. Pat. Nos. 3,589,578 and 4,031,307, each incorporated by reference, such as guar gums containing cationic trialkylammonium groups. Guar gums modified with a salt (e.g. chloride) of 2,3-epoxypropyltrim-ethylammonium are used, for example.

(5) Polymers comprising piperazinyl units and divalentalkylene or hydroxyalkylene radicals containing straight or branched chains, optionally interrupted by oxygen, sulphur or nitrogen atoms or by aromatic or hetero-cyclic rings, as well as the oxidation and/or quaternization products of these polymers.

(6) Water-soluble polyamino amides prepared, in particular, by polycondensation of an acidic compound with a polyamine; these polyamino amides can be crosslinked with an epihalohydrin, a diepoxide, a dianhydride, an un-saturated dianhydride, a bis-unsaturated derivative, a bis-halohydrin, a bis-azetidinium, a bis-haloacyidiamine, a bis-alkyl halide or, alternatively, with an oligomer resulting from the reaction of a difunctional compound that is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized.

(7) The polyamino amide derivatives resulting from the condensation of polyalkylene polyamines with polycarboxylic acids followed by alkylation with difunctional agents. Mention may be made, for example, of adipicacid/dialkylaminohydroxyalkyldialkylenetriamine polymers in which the alkyl radical contains from 1 to 4 carbon atoms and desirably denotes methyl, ethyl or propyl. Among these derivatives, particular examples include the adipic acid/dimethylaminohydroxypropyl/diethylenetriamine polymers sold under the name "Cartaretine F, F4 or F8" by the Sandoz company.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between about the polyalkylenepolyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Such polymers are described, in particular, in U.S. Pat. Nos. 3,227,615 and 2,961,347, each incorporated herein by reference. Polymers of this type are sold in particular under the name "HERCOSEFT 57" by the company Hercules Inc. or, alternatively, under the name "PD 170" or "DELSETTE 101" by the company Hercules in the case of the adipicacid/epoxypropyl/diethylenetriamine copolymer.

(9) Cyclopolymers of alkyldiallylamine or of dialkyl-diallylammonium, such as the homopolymers or copolymers. Among these polymers, mention may be made, more particularly, of the dimethyldiallylammonium chloride homopolymer sold under the name "MERQUAT 100" by the company Calgon and its homologues of low weight average molecular mass.

(10) Quaternary diammonium polymers containing aliphatic, alicyclic or arylaliphatic radicals containing from 1 to 20 carbon atoms or lower hydroxyalkylaliphatic radicals, heterocycles optionally containing a second hetero atom other than nitrogen, or, alternatively, a linear or branched C1-C6 alkyl radical substituted with a nitrile, ester, acyl or amide group. These polymers generally have a number-average molecular mass ranging from 1000 to 100,000.

(11) Quaternary polyammonium polymers as are described, in particular, in European patent application EP-A-122,324, incorporated here-in by reference. Among these products, mention may be made, for example, of "MIRAPOL® A 15", "MIRAPOL® AD1", "MIRAPOL® AZ1" and "MIRAPOL® 175" sold by the company Miranol.

(12) Homopolymers or copolymers derived from acrylic or methacrylic acids and containing units. The comonomer(s) that can be used in the preparation of the corresponding copolymers belong to the family of acrylamides, methacrylamides, diacetone acrylamides, acrylamides and methacrylamides substituted on the nitrogen with lower alkyls, alkyl esters, acrylic or meth-acrylic acids, vinylpyrrolidone or vinyl esters.

(13) Quaternary polymers of vinylpyrrolidone and of vinylimidazole, such as, for example, the products sold under the names LUVIQUAT® FC 905, FC 550 and FC 370 by the company BASF.

(14) Polyamines such as POLYQUART® H sold by Henkel under the reference name "Polyethylene glycol (15) tallowpolyamine" in the CTFA dictionary.

(15) Polymers of methacryloyloxy(C1-C4)alkyltri(C1-C4)alkylammonium salts such as the polymers obtained by homopolymerization of dimethylaminoethyl meth-acrylate quaternized with methyl chloride, or by copolymerization of acrylamicle with dimethylaminoethylmethacrylate quaternized with methyl chloride, the ho-mo- or copolymerization being followed by crosslinking with a compound containing olefinic unsaturation, in particular, methylenebisacrylamide. A crosslinked acrylamide/methacryloyloxyethyltrimethylammoniumchloride copolymer (20/80 by weight) in the form of a dispersion containing 50 weight percent of the copolymer in mineral oil can be used more particularly. This dispersion is sold under the name "SALCARE® SC 92" by Allied Colloids. A crosslinked methacryloyloxyeth-yltrimethylammonium chloride homopolymer containing about 50 weight percent of the homopolymer in mineral oil or in a liquid ester can also be used. These dispersions are sold under the names "SALCARE® SC 95 and SC 96" by the company Allied Colloids.

Other cationic polymers that can be used in the context of the invention are polyalkyleneimines, in particular, polyethyleneimines, polymers containing vinylpyridine or vinylpyridinium units, condensates of polyamines and of epichlorohydrin, quaternary polyureylenes and chitin derivatives. Among all the cationic polymers that can be used in the context of the present invention, it is desired to use cyclopolymers, in particular, homopolymers of a diallyidimethylammonium salt and copolymers of a diallyidim-ethylammonium salt and of acrylamide, in particular, the chlorides, sold under the names MERQUAT® 100, MERQUAT® 550" and MERQUAT® S by the company Calgon, optionally crosslinked homopolymers and copolymers sold by the company Allied Colloids as a 50% solution in mineral oil, under the trade names SALCARE SC92 (crosslinked co-polymer of methacryloyloxyethyltrimethylammoniumchloride and of acrylamide) and Salcare SC95 (crosslinked homopolymer of methacryloyloxyethyltrimethylammonium chloride), copolymers of vinylpyrrolidone and of a vinylimidazoline salt, such as the products sold by BASF under the names LUVIQUAT® FC 370, LUVIQUAT® FC 550, LUVIQUAT® FC 905 and LUVIQUAT® HM-552.

Still other cationic polymers suitable for use in the invention are those made according to U.S. Pat. Nos. 6,323,306 and 6,084,045, incorporated herein by reference. The '306 patent teaches methods of making high molecular weight, water soluble crosslinked cationic polymers. The '045 patent teaches methods of making water swellable but water insoluble cationic polymers comprising units derived from diallylic quaternary ammonium salt monomers.

Active Ingredients

The treating agents, active agents and medicaments useful herein are selected generally from the classes of medicinal agents, i.e., pharmaceutically active agents, and cosmetic agents. Substantially any agent of these two classes of materials that is a solid at ambient temperatures may be used in a composition or method of the present invention. Medicaments that are liquid at ambient temperatures, e.g. nitroglycerin, can be used in a composition of this invention.

The medicaments or treating agents, when used in the system of this invention, are released in a "controlled release" manner. This means that, since they are distributed throughout the composition of the invention, as the body breaks down the composition, the medicament is released into the body over the time period the body takes to completely break down the composition.

Exemplary medicinal agents include agents for treating cardiovascular conditions such as chlorothiazide (diuretic), propranolol (antihypertensive), hydralazine (peripheral vasodilator), isosorbide or nitroglycerin (coronary vasodilators), metoprolol (beta blocker), procainamide (antiarrythmic), clofibrate (cholesterol reducer) or coumadin (anticoagulant); agents for treating internal conditions such as conjugated estrogen (hormone), tolbutamide (antidiabetic), levothyroxine (thyroid conditions), propantheline (antispasmodic), cimetidine (antacid), phenyl propanolamine (antiobesity), atropine or diphenoxalate (antidiarrheal agents), docusate (laxative), or prochlorperazine (antinauseant); agents for treating mental health conditions such as haloperidol or chlorpromazine (tranquilizers), doxepin (psychostimulant), phenyloin (anticonvulsant), levo dopa (antiparkinism), benzodiazepine (antianxiety) or phenobarbital (sedative); anti-inflammatory agents such as fluorometholone, acetaminophen, phenacetin, aspirin, hydrocortisone, or predisone; anti-histamines such as diphenhydramine hydrochloride or dexchlorpheniramine maleate; antibiotics such as sulfanilamide, sulfamethizole, tetracycline hydrochloride, penicillin and its derivatives, cephalosporin derivatives or erythromycin; chemotherapeutic agents such as sulfathiazole, doxorubicin, cisplatin or nitrofurazone; topical anaesthetics such as benzocaine; cardiac tonics such as digitalis or digoxin; antitussives and expectorants such as codeine phosphate, dextromethorphan or isoproterenol hydrochloride; oral antiseptics such as chlor hexidine hydrochloride or hexylresorcinol; enzymes such as lysozyme hydrochloride or dextronase; birth control agents such as estrogen; ophthalmic treating agents such as timolol or gentamycin, and the like. In addition, medicinal treating agents may also include whole proteins such as the VP3 capsid protein (also known as the VPThr and VP1 capsid proteins in other nomenclature systems) of foot-and-mouth disease virus described in U.S. Pat. No. 4,140,763 as being useful as the active ingredient in a vaccine against foot-and-mouth disease, insulin or interferon; polypeptide treating agents such as endorphins, human growth hormone, or bovine growth hormone, or still lower molecular weight polypeptides or conjugates of those polypeptides linked protein carriers. Exemplary cosmetic agents include sunscreens such as p-dimethylaminobenzoic acid or glyceryl p-aminobenzoate, a skin softener such as urea, keratolytic agents such as salicylic acid; acne treating agents such as benzoyl peroxide or sulfur; perfumes, and the like. Nutritional agents such as vitamins and/or minerals like riboflavin and iron, respectively, may also comprise useful treating agents herein.

The treating agent or medicament may be used singly or as a mixture of two or more such agents.

One or more adjuvants may also be included with a treating agent, and when so used, an adjuvant is included in the meaning of the phrase "treating agent" as that phrase is used herein. Exemplary of useful adjuvants are chelating agents such as ethylenediaminetetracetic acid (EDTA) that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

The treating agent is or medicament present in the compositions of this invention in an amount that is sufficient to prevent, cure and/or treat a condition for a desired period of time for which the composition of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the animal in which it is used, and the body weight of that animal. Consequently, effective amounts of treating agents may not be defined for each agent. Thus, an effective amount is that amount which in a composition of this invention provides a sufficient amount of the treating agent to provide the requisite activity of treating agent in or on the body of the treated animal for the desired period of time, and is typically less than that amount usually used.

Since amounts of particular treating agents in the blood stream that are suitable for treating particular conditions are generally known, as are suitable amounts of treating agents used in cosmetics, it is a relatively easy laboratory task to formulate a series of controlled release compositions of this invention containing a range of such treating agents to determine the effective amount of such a treating agent for a particular composition of this invention. While the effective amount for all treating agents cannot be stated, typical compositions of this invention may contain about one microgram to about one gram of treating agent per dose administered.

Moisturizers

Moisturizers may be included with the delivery system blend in order to deliver them directly to the body cavity tissues. Suitable moisturizers known in the art include vitamin E, aloe, stearic acid, cetyl alcohol, glyceryl stearate SE and polysorbate 20, alpha-hydroxy acid.

EXAMPLES

The following embodiments illustrate the invention in varying scope. All the following example formulations were tested for their thermogelation property by the inverting-flow test method. In this test method, vials containing the formulations are immersed into a water bath with different temperatures until they reach equilibrium, and are then inverted to see the flow behavior. A gel was defined as systems without notable flow by this method for at least 2 minutes. Thermogels according to this invention should be a gel at body temperatures, about 35° C.

Example 1

Water solutions containing 17.3 weight percent of PLURONIC® F127 and poly(diallyl dimethyl ammonium chloride) (PDADMAC, MW 400,000-500,000) of various concentrations with or without NaCl were tested for the gelation behavior in the temperature range 4-40° C. All the formulations were clear, homogeneous and stable. The results are summarized as following:

| | Weight percent Polyelectrolyte | |
|---|---|---|
| | without NaCl | with 1 wt percent NaCl |
| 1 | gels around 25° C. | gels around 36° C. |
| 2 | gels around 25° C. | gels around 31° C. |

-continued

| | Weight percent Polyelectrolyte | |
|---|---|---|
| | without NaCl | with 1 wt percent NaCl |
| 3 | gels around 26° C., but liquid again at 34° C. | gels around 22° C., and remains so |
| 4 | remains liquid | gels around 24° C., and remains so. |
| 5 | remains liquid | gels around 15° C., and remains so. |

Example 2

Water solutions containing 17.5 weight percent of PLURONIC® F127, 3.0 weight percent of poly(diallyl dimethyl ammonium chloride) (PDADMAC, MW 400,000-500,000), 0.9 weight percent of NaCl and 0.1 weight percent of citric acid had a pH of 3.3. The solutions were clear, homogeneous and stable, and they were flowing liquid at room temperature (22° C.), but geled at 35° C.

It is desired that the bioadhesive system of this invention have from a positive amount to about 20 weight percent of an intrinsically cationic bioadhesive polymer, and from about 5 to 50 weight percent of a thermogelling polymer with the balance water and any medicaments and/or moisturizers. More particularly the bioadhesive can be present in an amount between a positive amount and 10 weight percent and the thermogelling polymer in an amount between about 8 and 25 weight percent with the balance water and any medicaments and/or moisturizers. Still more particularly, the thermogelling polymer may be present in an amount between about 15 and 25 weight percent with the balance water and any medicaments and/or moisturizers.

As can be seen from the examples, a salt in an effective amount improves the gelling behavior of the composition and it's desired that a salt be present in an amount between a positive amount and 1.5 weight percent, particularly around 1 weight percent. Although the Examples were carried out using sodium chloride (NaCl) as the salt, one skilled in the art could surmise that other similar salts like potassium chloride, magnesium chloride and others would perform similarly.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention.

What is claimed is:

1. An aqueous, temperature responsive composition that comprises a polyoxypropylene-polyoxyethylene block copolymer in an amount from about 5 wt. % to about 50 wt. %, at least one intrinsically cationic bioadhesive polymer in a positive amount up to about 20 wt. %, a salt present in an amount between a positive amount and 1.5 wt. %, and water, wherein the aqueous, temperature responsive composition changes from a liquid at about 22° C. to a gel at a temperature of about 35° C.

2. The composition of claim 1, wherein the polyoxypropylene-polyoxyethylene block copolymer is present in an amount from about 8 wt. % to about 25 wt. %.

3. The composition of claim 1, wherein the polyoxypropylene-polyoxyethylene block copolymer is present in an amount from about 15 wt. % to about 25 wt. %.

4. The composition of claim 1, wherein the bioadhesive polymer is present in a positive amount up to about 10 wt. %.

5. The composition of claim 1, wherein the bioadhesive polymer contains at least one ammonium group in a main chain, side chain, pendant chain, or combinations thereof.

6. The composition of claim 1, wherein the bioadhesive polymer is synthetic.

7. The composition of claim 1, wherein the bioadhesive polymer is a quaternary polyammonium, quaternary polyamino, or quaternary polyamine polymer.

8. The composition of claim 7, wherein the bioadhesive polymer is a polymer of an alkyldiallylamine or dialkyl-diallylammonium.

9. The composition of claim 8, wherein the bioadhesive polymer is a polymer of dimethyldiallylammonium chloride.

10. The composition of claim 7, wherein the bioadhesive polymer is poly(dimethylamine-co-epichlorohydrin).

11. The composition of claim 1, further comprising at least one moisturizer.

12. The composition of claim 1, wherein the salt is sodium chloride, potassium chloride, or magnesium chloride.

13. The composition of claim 1, further comprising at least one medicament selected from the group consisting of agents for treating infection and menstruation disorders, agents for treating cardiovascular conditions, agents for treating internal conditions, agents for treating mental health conditions, anti-inflammatory agents, chemotherapeutic agents, cardiac tonics, expectorants, oral antiseptics, enzymes, birth control agents, ophthalmic treating agents, and combinations thereof.

14. The composition of claim 1, wherein the polyoxypropylene-polyoxyethylene block copolymer has the formula:

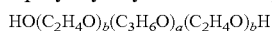

wherein a and b are integers such that the polyoxypropylene block has an average molecular weight of at least 900 as determined by hydroxyl number and the polyoxyethylene block comprises at least 60% weight percent of the copolymer, and wherein the copolymer has a total average molecular weight of at least 5000.

15. The composition of claim 1, wherein the polyoxypropylene-polyoxyethylene block copolymer comprises a polyoxypropylene-polyoxyethylene block copolymer of ethylene diamine.

16. An aqueous, temperature responsive composition that comprises at least one polyoxypropylene-polyoxyethylene block copolymer in an amount from about 5 wt. % to about 50 wt, %, at least one intrinsically cationic bioadhesive polymer in a positive amount up to about 20 wt. %, a salt, and water, wherein the bioadhesive polymer is a polymer of an alkyl-diallylamine or dialkyl-diallylammonium, and wherein the aqueous, temperature responsive composition changes from a liquid at about 22° C. to a gel at a temperature of about 35° C.

17. The composition of claim 16, wherein the polyoxypropylene-polyoxyethylene block copolymer has the formula:

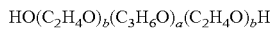

wherein a and b are integers such that the polyoxypropylene block has an average molecular weight of at least 900 as determined by hydroxyl number and the polyoxyethylene block comprises at least 60% weight percent of the copolymer, and wherein the copolymer has a total average molecular weight of at least 5000.

18. The composition of claim 16 wherein the polyoxypropylene-polyoxyethylene block copolymer comprises a polyoxypropylene-polyoxyethylene block copolymer of ethylene diamine.

* * * * *